(12) United States Patent
Monmont et al.

(10) Patent No.: US 7,640,133 B2
(45) Date of Patent: *Dec. 29, 2009

(54) METHOD, APPARATUS AND SYSTEM FOR CHARACTERIZING TWO PHASE FLUID FLOW IN AN INJECTION WELL

(75) Inventors: Franck Bruno Jean Monmont, Caldecote (GB); Herve Ohmer, Houston, TX (US); Gary Martin Oddie, St. Neots (GB); Allan Peats, Okotoks (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/109,848

(22) Filed: Apr. 25, 2008

(65) Prior Publication Data

US 2009/0271129 A1 Oct. 29, 2009

(51) Int. Cl.
*G06F 15/00* (2006.01)
*G01K 7/00* (2006.01)
*G01F 1/00* (2006.01)
*E21B 47/10* (2006.01)

(52) U.S. Cl. .................... 702/136; 702/50; 73/861.04; 73/152.18

(58) Field of Classification Search ............ 702/45, 702/50, 136; 73/861.04
See application file for complete search history.

(56) References Cited

U.S. PATENT DOCUMENTS 4,931,687 A * 6/1990 Thayer .................. 313/231.01
6,502,456 B1 * 1/2003 Chen ....................... 73/152.46

OTHER PUBLICATIONS

Hong, K.C. et al., "Best Practice for the Distribution and Metering of Two-Phase Steam", Paper, SPE 35422, Aug. 1997.
SPE 68830, "Orifice Meters for Steam Injector Monitoring", Castrup, S., 2001.
Crighton, D.G. et al, "Modern Methods in Analytical Acoustics", Lecture Notes Springer Verlag, 1992.
Crowe, C.T. et al, "Metering Low-Quality Steam-Water Flows", Paper UCRL-52271, 1977.
Lumbroso, H., "Thermodynamique", McGraw-Hill (1989).

* cited by examiner

*Primary Examiner*—Bryan Bui
(74) *Attorney, Agent, or Firm*—Jay P. Sbrollini; Wayne I. Kanak

(57) ABSTRACT

A method and corresponding system is provided for determining fluid properties of a two phase fluid flowing through various portions of a wellbore. Specifically, the method and corresponding system determines fluid properties (e.g. enthalpy flux) of the two phase fluid flowing upstream of the injector portion of the wellbore as well as fluid properties (e.g., mass flow rate and enthalpy flux) of the two phase fluid at various measurement locations along the injector.

16 Claims, 4 Drawing Sheets

METHOD, APPARATUS AND SYSTEM FOR CHARACTERIZING TWO PHASE FLUID FLOW IN AN INJECTION WELL

CROSS-REFERENCE TO RELATED APPLICATION

This application is related to application Ser. No. 12/109,631, filed Apr. 25, 2008 entitled "Apparatus and Method for Characterizing Two Phase Fluid Flow".

BACKGROUND OF THE INVENTION

1. Field of the Invention

This invention relates broadly to the analysis of two phase fluid flow. More particularly this invention relates to a method, apparatus and system for characterizing two phase fluid flow into and through an injection well.

2. Description of Related Art

There are many petroleum bearing formations from which oil cannot be recovered by conventional means because the oil is so viscous that it will not flow from the formation to a conventional oil well. Examples of such formations are the bitumen deposits in Canada and the United States and the heavy oil deposits in Canada, the United States, and Venezuela. In these deposits, the oil is so viscous under the temperatures and pressures prevailing within the formations that it flows very slowly (or not at all) in response to the force of gravity. Heavy oil is an asphaltic, dense (low API gravity), and viscous oil that is chemically characterized by its contents of asphaltenes. Most heavy oil is found at the margins of geological basins and is thought to be the residue of formerly light oil that has lost its light molecular weight components through degradation by bacteria, water-washing, and evaporation.

Heavy oil is typically recovered by injecting superheated steam into an oil reservoir, which reduces the oil's viscosity and increases the reservoir pressure through displacement and partial distillation of the oil. Steam may be injected continuously utilizing separate injection and production wells. Alternatively, the steam may be injected in cycles such that the well is used alternatively for injection and production (a "huff and puff" process).

A large percentage of heavy oil recovery methods use steam injection with different well arrangements, but fail to provide adequate support for monitoring the Fluid flow into and through the injector well for control and optimization of the injection process.

BRIEF SUMMARY OF THE INVENTION

A method and corresponding system is provided for determining fluid properties of a two phase fluid flowing through various portions of a wellbore. Specifically, the method and corresponding system determines fluid properties (e.g. enthalpy flux via density, pressure, and temperature) of the two phase fluid flowing upstream of the injector portion of the wellbore (hereinafter 'injector') as well as fluid properties (e.g. mass flow rate and enthalpy flux via pressure and temperature) of the two phase fluid at various measurement locations along the injector.

The method and corresponding system of the present invention enable the properties of the two phase fluid flowing, into and through the injector well to be monitored for better control and optimization of the injection process.

The fluid properties of the two phase fluid flowing upstream of the injector is determined by measuring temperature, pressure, and density of the two phase fluid upstream of the injector. These measurements are used to calculate the fluid's vapor phase fraction and homogeneous mass density. The homogeneous mass density is used in conjunction with energy and mass continuity equations to estimate the volume flow rate and mass flow rate for the vapor phase and liquid phase of the two phase fluid. The enthalpy flux of the two phase fluid is then calculated based on the mass flow rate of the vapor phase and liquid phase of the two phase fluid, as well as known enthalpy values for the vapor and liquid phases of the two phase fluid at the measured temperature and pressure.

The fluid properties of the two phase fluid along the injector are determined by measuring temperature, pressure, and velocity of the fluid at a plurality of measurement locations along the injector. A vapor phase fraction is estimated for each measurement location along the injector based on the measured temperature and pressure and assuming phase equilibrium. The calculation of each vapor phase fraction is preferably based in part on the Clapeyron relationship, the equation of state for water vapor, and the ideal gas law. The calculated vapor phase fraction for each measurement location along the injector allows for fluid density collections in the overall energy calculations. A mass balance equation is used in Conjunction with the vapor phase fraction, and the measured temperature and pressure, to determine the mass flow rate and enthalpy flux of the two phase fluid at each measurement location.

In the preferred embodiment, measurements are taken along the injector with a toot that houses a temperature sensor, and a pressure sensor. The measurements taken by the toot are communicated to a surface-located data processing means for storage and processing. The tool is movable to the various measurement locations along the injector by a positioning means, which is preferably realized by coiled tubing that supports the toot at its downhole end. The coiled tubing and tool are conveyed downhole and deployed through a heel and injector portion of the wellbore. The coiled tubing may be pushed/pulled forward or backward in order to position the tool at various locations along the injector portion of the wellbore.

In another aspect of the invention, an apparatus (and corresponding method) for determining fluid properties of a two phase fluid includes a restriction element (e.g., orifice plate or nozzle) along the flow path of the two phase fluid. At least one temperature sensor measures temperature of the two phase fluid flowing through the restriction element. Pressure sensors measure the pressure drop across the restriction element. Time-of-flight measurements of Sonic pulses passing through the two phase fluid are made. The speed of sound within the two phase fluid is calculated from the time-of-flight measurements. At least one fluid property (e.g., a vapor phase fraction and possibly other properties derived therefrom) of the two phase fluid is calculated from the measured pressure drop, the measured temperature, and the calculated speed of sound. The apparatus (and methodology) can be used to calculate fluid properties (e.g., vapor phase fraction and properties calculated therefrom) of a two phase fluid upstream of the injector as described herein.

DETAILED DESCRIPTION OF THE INVENTION

Figure 1A:
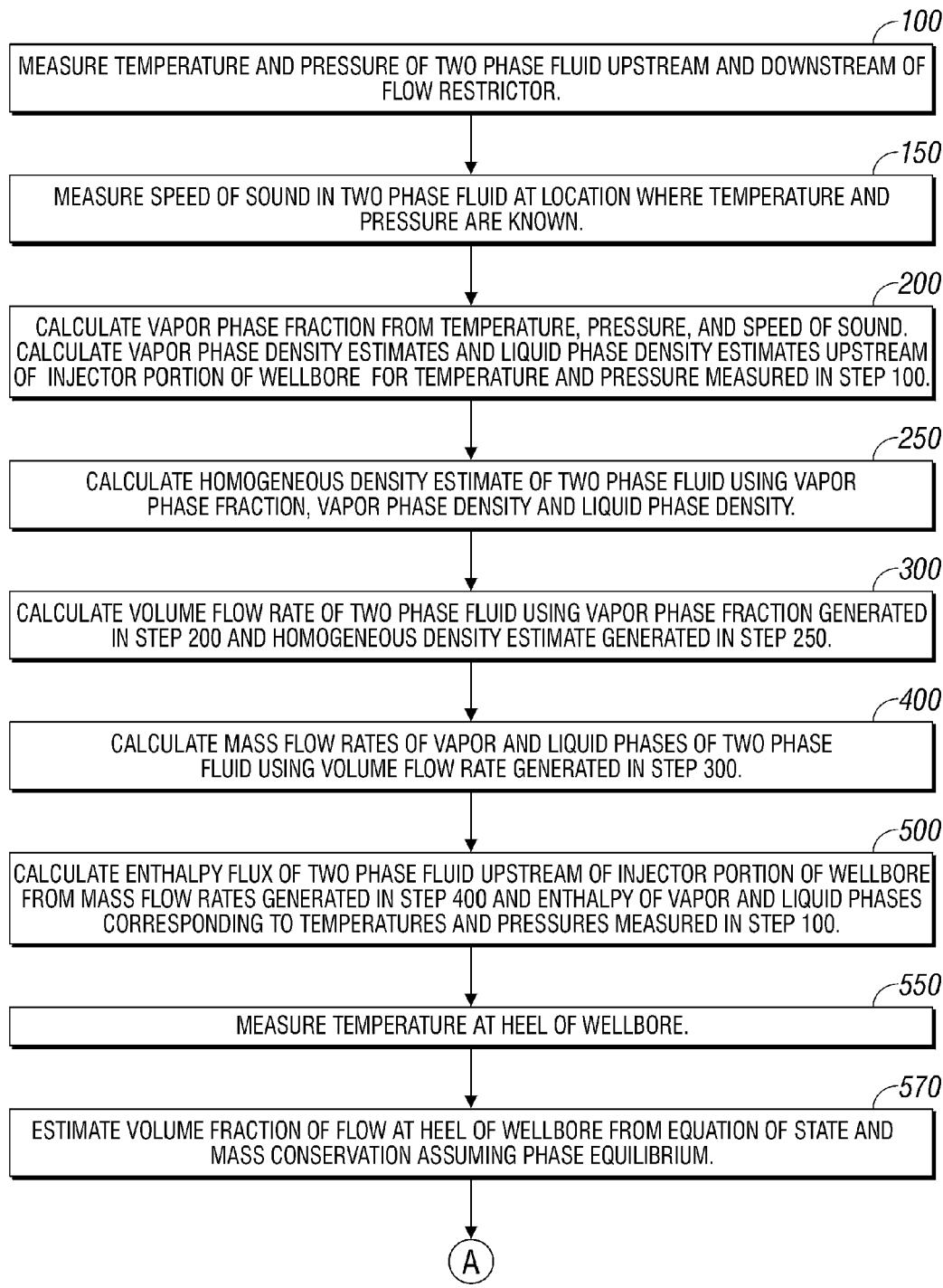
FIGS. 1A and 1B, collectively, is a flow chart outlining the methodology for determining fluid properties of a two phase fluid flowing through an injector well in accordance with the present invention.
Figure 1B:
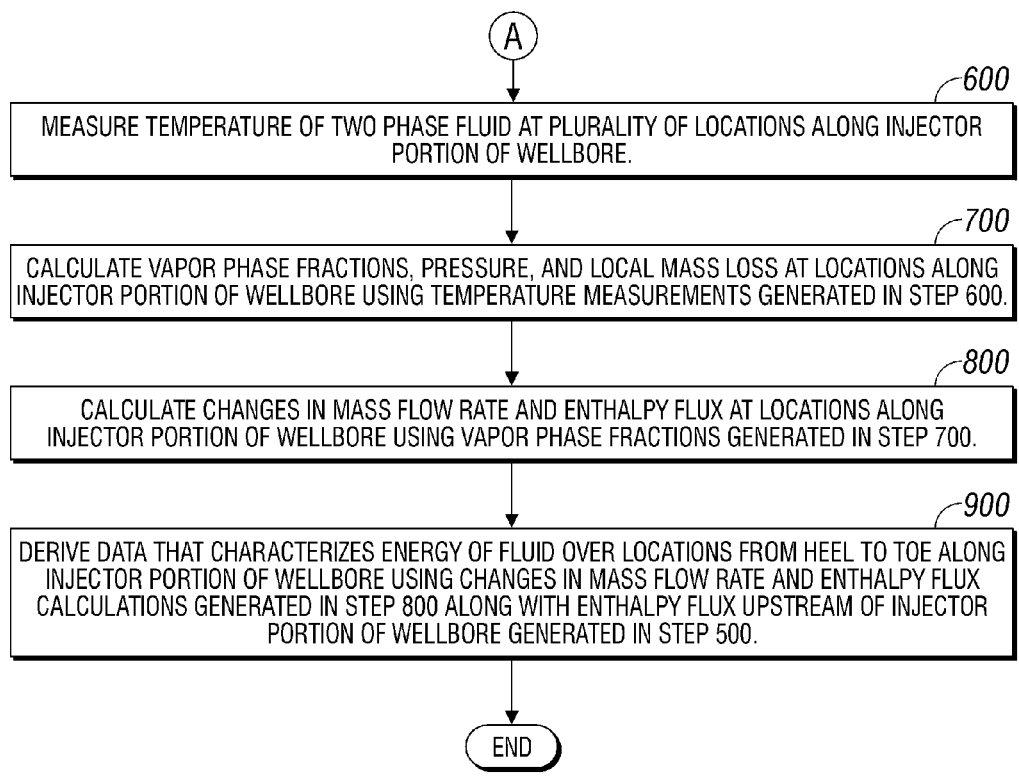

Turning to FIGS. 1A and 1B, there is shown a method for determining a number of fluid properties of a two phase fluid (e.g., steam and water) flowing upstream of an injector portion of a wellbore (FIG. 3) as well as a number of fluid properties of the two phase fluid along the injector portion of the wellbore.

The enthalpy (heat content) of the two phase fluid upstream of the injector portion the wellbore is given by the following equation:

$$h_t = m_v h_v(T,P) + m_l h_l(T,P) \quad (1)$$

where $m_v$ is the mass of the vapor phase of the two phase fluid,
$h_v(T,P)$ is the enthalpy of the vapor phase of the two phase fluid at temperature T and pressure P,
$m_l$ is the mass of the liquid phase of the two phase fluid, and
$h_l(T,P)$ is the enthalpy of the liquid phase of the two phase fluid at temperature T and pressure P.

It is assumed that the vapor and liquid phases of the two phase fluid are in equilibrium alone the wellbore, and thus that that their respective enthalpy values vary as a function of the pressure and temperature only.

The enthalpy flux is given by Equation 1 as follows:

$$h_t^\& = m_v^\& h_v(T,P) + m_l^\& h_l(T,P) \quad (2)$$

where $m_v^\&$ is the mass flow rate of the vapor phase of the two phase fluid,
and $m_l^\&$ is the mass flow rate of the liquid phase of the two phase fluid.

The methodology of FIGS. 1A and 1B begins in step 100 by measuring temperature and pressure of the two phase fluid upstream and downstream of a flow restrictor. Such temperature and pressure measurements may be carried out by any means known in the art, such as, for example, via a thermocouple or a resistance temperature detector (RTD) probe for temperature or a pressure transducer for pressure.

In step 150, the speed of sound in the two phase fluid is measured at the location where temperature and pressure are known.

In step 200, the vapor phase fraction is calculated from the temperature, pressure and speed of sound. Vapor phase density estimates $\rho_v$ and liquid phase density estimates $\rho_l$ are then calculated upstream of the injector portion of the wellbore for the temperature and pressure measured in step 100. This calculation is made from known equations of state (e.g. steam tables).

In step 250, a homogeneous density estimate $\rho$ is now calculated from the vapor phase fraction, $\alpha$, and $\rho_v$, and $\rho_l$ according to the relationship $\rho = \rho_v \alpha + \rho_l(1-\alpha)$. A vapor phase fraction $\alpha$ of the two phase fluid is calculated by measuring the time-of-flight of sound pulses traveling through the fluid as described below with respect to the metering device of FIG. 4. A homogeneous density estimate $\rho_1$ upstream of the restriction element is derived from the vapor phase density estimate $\rho_v$ and liquid phase density estimate $\rho_l$ for the fluid upstream of the restriction element. A homogeneous density $\rho_2$ at the vena contracta of the restriction element is derived from the vapor phase density estimate $\rho_v$ and liquid phase density estimate $\rho_l$ for the fluid at the vena contracta of the restriction element.

In step 300, the vapor phase fraction $\alpha$ generated in step 200 and the homogeneous density estimate $\rho$ generated in step 250 are used to calculate a volume flow rate $Q_t$ of the two phase fluid upstream of the injector portion of the wellbore. In the preferred embodiment, the calculations of step 300 are derived from the energy and mass conservation equations representing the flow across the restriction element as follows:

$$u_2^2 - u_1^2 = 2(h_1 - h_2) = 2\left(e_1(T) + \frac{p_1}{\rho_1} - e_2(T) - \frac{p_2}{\rho_2}\right) \quad (3)$$

$$\rho_1 u_1 A_1 = \rho_2 u_2 A_2 \quad (4)$$

where
$u_1$ is the homogeneous velocity of the two phase fluid upstream from the restriction element;
$u_2$ is the homogeneous velocity of the two phase fluid at the vena contracta of the restriction element;
$h_1$ is the enthalpy at the inlet of the restriction element;
$h_2$ is the enthalpy at the outlet of the restriction element;
$e_1(T)$ is the internal energy of the flow (constant pressure) at the inlet of the restriction element;
$e_2(T)$ is the internal energy of the flow (constant pressure) at the outlet of the restriction element;
$p_1$ is the pressure upstream of the restriction element;
$p_2$ is the pressure at the vena contracta of the restriction element;
$\rho_1$ is the homogeneous density upstream of the restriction element;
$\rho_2$ is the homogeneous density at the vena contracta of the restriction element;
$A_1$ is the cross sectional area of the two phase fluid flow upstream of the restriction element; and
$A_2$ is the cross-sectional area of the two phase fluid flow at the vena contracta of the restriction element.

Substituting Equation 4 into Equation 3 and solving for $u_2$ yields:

$$u_2 = C_d \sqrt{\frac{2(h_1 - h_2)}{1 - \frac{\rho_2^2 A_2^2}{\rho_1^2 A_1^2}}} \quad (5)$$

where $C_d$ is a discharge coefficient.

The volume flow rate $Q_t$ of the two phase fluid can calculated from Equation 5 as follows:

$$Q_t = u_2 A_2. \quad (6)$$

In step 400, the mass flow rates $m_v^\&$, $m_l^\&$ for the vapor and liquid phases of the two phase fluid upstream of the injector portion of the wellbore are calculated as follows:

$$m_v^\& = (\alpha \rho_v)_2 Q_t \quad (7)$$

$$m_l^\& = (\rho_l(1-\alpha))_2 Q_t. \quad (8)$$

In step 500, the mass flow rates $m_v^\&$, $m_l^\&$ of step 400 along with the enthalpy of the vapor and liquid phases $h_v(T,P)$, $h_l(T,P)$ for the temperatures and pressures measured in step 100 are used to calculate the enthalpy flux $h_t^\&$ of the two phase fluid upstream of the injector portion of the wellbore in accordance with Equation 2 above.

In step 550, the temperature at the heel of the wellbore is measured.

In step 570, the volume fraction of the flow is estimated from the equation of state (e.g. Clausius-Clapeyron) and mass conservation, assuming local phase equilibrium.

In step 600, the temperature of the two phase fluid is measured at a plurality of locations along the injector portion of the wellbore.

In step 700, the temperature measurements of step 600 are used to derive vapor phase fractions, pressure, and local mass loss for each given location. In calculating the vapor phase fraction $\alpha_t$ for the given location, it is assumed that the two phases of the fluid are in equilibrium. By combining the Clapeyron relationship and the equation of state for a two phase fluid, it can be shown that the change in volume of 1 mole of saturated vapor dv due to a change of temperature dT and pressure dp is:

$$dv = \frac{1}{P}\left(R - \frac{L_v}{T}\right)dT \qquad (9)$$

where $L_v$ is the Latent heat of vaporization and is a function of temperature T only;
R is a known constant; and
P and T are measured pressure and temperature values, respectively.

Therefore, if $V_l$ is the volume occupied by one mole of liquid phase of the fluid at temperature T and pressure P, and if one mole of vapor occupies volume $V_v$ at temperature T and pressure P, then it will occupy volume $V_v$+dv at pressure. P+dp, and temperatures T+dT. If the volume fraction of the mole of vapor phase of the two phase fluid at temperature T and pressure P is $$\alpha_1 = \frac{V_v}{V_v + V_1},$$

the volume fraction of the mole of vapor phase of the two phase fluid at temperature T+dT and pressure P+dp will be $$\alpha_2 = \frac{V_v + dv}{V_v + dv + V_1}.$$

This estimation assumes that the change in volume of the liquid water is negligible, and that the vapor portion of the fluid behaves like an ideal gas. As the compressibility of the liquid phase is very small, the assumption is not a significant source of error. If desired, a more refined equation of state for the two phase fluid may be used to compute the compressibility factors of the liquid and vapor phases and thus the relative change in volume of the two phases.

Figure 2:
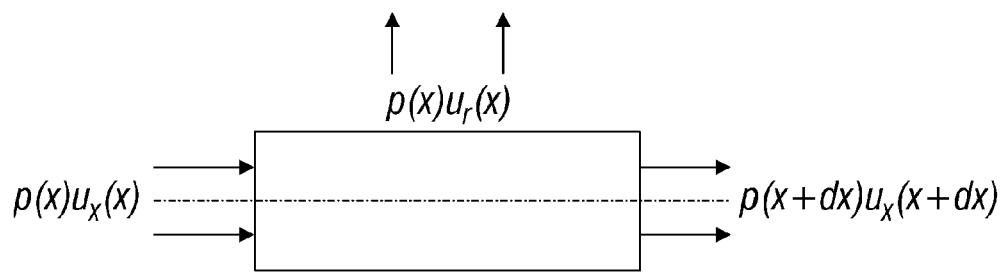
FIG. 2 is a diagram illustrating a unit volume of a wellbore with a corresponding mass balance equation.

In step 800, the vapor phase fractions generated in step 700 are used to calculate the changes in mass flow rate and enthalpy flux at the measurement locations along the injector portion of the wellbore. Consider the mass balance and the energy balance of a unit volume as shown in FIG. 2. The unit volume is modeled as a cylinder of radius r bounded by two opposing ends. One end of the cylinder (the entrance of the unit volume) lies at position x along the injector portion of the wellbore, while the other end of the cylinder (the exit of the unit volume) lies at position x+dx along the injector portion of the wellbore. The length of the cylindrical unit volume is dx. The fluid arriving at the entrance of the unit volume includes two parts: one part flows through the cylindrical unit volume to the exit of the unit volume along the x direction, and the other part is injected radially through the annular sidewall of the cylinder of the unit volume into the formation.

Applying a mass balance to this unit volume produces the following equation:

$$((\rho(x+dx)u_x(x+dx) - \rho(x)u_x(x))\cdot\pi r^2) + ((\rho(x)u_r(x))\cdot 2\pi r dx) = 0 \qquad (10)$$

where $\rho(x)$ is the homogeneous density of the two phase fluid at the entrance of the unit volume (at position x);
$\rho(x+dx)$ is the homogeneous density of the two phase fluid at the exit of the unit volume (at position x+dx);
$u_x(x)$ is the homogeneous velocity of the two phase fluid along the x direction of the injector well at the entrance of the unit volume;
$u_x(x+dx)$ is the homogeneous velocity of the two phase fluid along the x direction of the injector at the exit of the unit volume; and
$u_r(x)$ is the uniform radial velocity of the two phase fluid along the unit volume of length dx.

Applying an energy balance on the unit volume yields the following equation:

$$\rho(x+dx)u_x(x+dx)h(x+dx) - \rho(x)u_x(x)h(x) + \qquad (11)$$
$$\frac{1}{2}(\rho(x+dx)(u_x(x+dx))^3 - \rho(x)(u_x(x))^3) = -\rho(x)u_r(x)h(x)\cdot 2\frac{dx}{r}$$

where h(x) is the total enthalpy of the two phase fluid at the entrance of the unit volume; and
h(x+dx) is the total enthalpy of the two phase fluid at the exit of the unit volume.

This assumes that the void fraction (and enthalpy) of the fluid leaving the wellbore element is the same as the void fraction (and enthalpy) remaining in the wellbore element.

Equations 11 and 12 assume that the vapor and the liquid phases of the fluid travel across the unit volume with the same homogeneous velocity $u_x$ with no slip. Such assumptions are more accurate in the event that the two phases are mixed upstream of the unit volume. In the preferred embodiment, such mixing is accomplished by a static mixer disposed upstream of the unit volume.

Substituting Equation 10 into Equation 11 gives:

$$\frac{\rho(x+dx)}{\rho(x)}u_x(x+dx)\left(e(x+dx) - \frac{1}{2}u_x(x+dx)^2 - h(x)\right) = \qquad (12)$$
$$\frac{1}{2}u_x(x)^3 + \frac{\rho(x+dx)}{\rho(x)}u_x(x+dx).$$

In Equation 12, the measured quantities are homogeneous velocity (at x and x+dx) and temperature (at x and x+dx); the inferred quantities are energy enthalpy, and void fraction (density) at both end points of the wellbore element. Note that the measurements of homogeneous velocity $u_x$ alone the injector portion of the wellbore can be carried out by a turbine flow meter or other instrument known in the art.

In step 900, the changes in mass flow rate and enthalpy flux calculations of step 800 along with the enthalpy flux of the two phase fluid upstream of the injector portion of the wellbore generated in step 500 are used to generate data that characterizes energy of the two phase fluid as it flows alone the injector portion of the wellbore.

Figure 3:
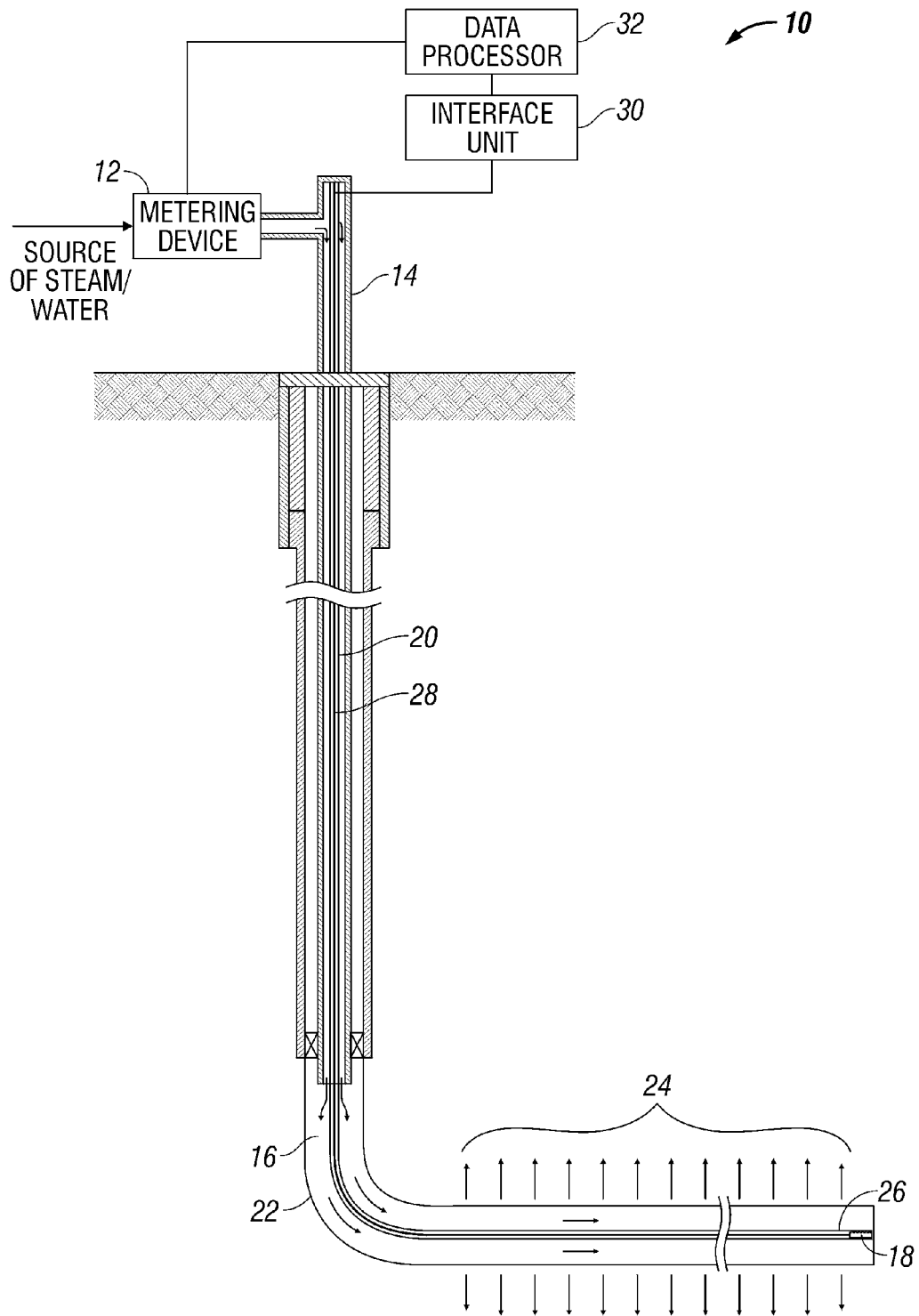
FIG. 3 is a schematic diagram of an illustrative embodiment of a system for determining the fluid properties of a two phase fluid flowing through an injector well in accordance with the present invention.

Turning to FIG. 3, there is shown a schematic diagram of an illustrative embodiment of a system 10 for determining fluid characteristics of a two phase fluid flowing through an injector wellbore in accordance with the present invention. The system includes a surface-located metering device 12 that is fluidly coupled between a source of two phase injection fluid (e.g. steam and water) and tubing 14 that extends downhole within an injector wellbore 16. The metering device 12 includes thermocouples (or temperature probes or other suitable sensors) for measuring temperatures of the two phase fluid before it enters the tubing 14, as well as pressure transducers for measuring pressures of the two phase fluid before it enters the tubing 14. The metering device 12 includes a data processing unit, which is preferably realized by a software programmed data processing system, that processes the temperature and pressure measurements provided by the temperature and pressure sensors of the metering device 12 (and possibly other input) to perform the calculations of steps 200 to 500 of FIG. 1 as described above in order to derive the enthalpy flux of the two phase fluid as it enters the tubing 14 for supply to the injector wellbore 16. It should be noted that the metering device 12 can be placed anywhere upstream of the wellhead, provided that local pressure and temperature are measured at the wellhead.

The system 10 also includes a tool 18 that houses a temperature sensor, a pressure sensor, and a flow rate meter (collectively referred to as the downstream measurement instruments) for measuring temperature, pressure and velocity, respectively, of the fluid at various measurement locations along the injector portion 24 of the wellbore 16. The tool 18 is conveyed to the various measurement locations along the wellbore 16 by positioning means, which is preferably realized by coiled tubing 20 that supports the tool 18 at or near its downhole end 26. The coiled tubing 20 and tool 18 are conveyed downhole through the tubing 14 and heel portion 22 of the wellbore 16 and into the injector portion 24 of the wellbore 16. The coiled tubing 20 comprises a continuous length of uniform outer diameter tubing (typically several hundred to several thousand feet), which is capable of being repeatedly coiled and uncoiled from a truckable spool, and which is capable of being repeatedly inserted into and withdrawn from the wellbore 16 and thus allows the tool 18 to be moved and positioned along the injector portion 24 of the wellbore 16 as desired. The coiled tubing 20 is typically, although not necessarily, manufactured of steel having a longitudinally welded seam. Being flexible, the coiled tubing 20 is particularly useful for horizontal injection well applications as shown in FIG. 3. The coiled tubing 20 includes one or more electrical cables 28 operably disposed inside the coiled tubing 20 and extending from the surface to the downhole end 26 and tool 18. The electrical cable(s) 28 carry electrical power for supply to the electrical components of the tool 18. The data representing the measurements of the downhole measurement instruments of the tool 18 are preferably carried to a surface-located interface unit 30 by the electrical cable(s) 28 (for example, by modulating power supply current carried by the electrical cable(s) 28) or other suitable data telemetry means. The interface unit 30 provides the measurement data communicated thereto from the tool 18 to a data processor 32. The data processor 32 stores the measurement data communicated from the tool 18 and carries out the calculations of steps 700 to 900 of FIG. 1 as described above to derive data that characterizes energy along the injector portion of the wellbore 16. The data processor 32 interfaces to the metering device 12 to provide for communication of data therebetween as needed. Note that the data processor 32 and metering device 12 are shown as distributed systems for simplicity of description. It is contemplated that the data processing functionality of the metering device 12 and the data processor 32 can be realized by a common data processing platform or other suitable architectures.

In a preferred embodiment of the present invention, the method of FIG. 1 and/or the system of FIG. 3 are used in conjunction with steam injection processes for heavy oil recovery. It such processes, a pressurized two phase fluid (e.g., under saturated steam and water) is supplied to an injector well for injection into the formation surrounding a portion of the injector well. The escaping fluid heats oil situated within the earth in close proximity to the injector well. As the oil is heated, it becomes more viscous and falls via gravity to one or more production wells disposed nearby. In commercial applications where injection fluid is injected to numerous injector wells in close proximity to one another adjacent a heavy oil deposit (e.g. where there may be well-to-well cross-resistivity), information regarding the fluid properties of the injection fluid (e.g., energy) along the injector wells is useful for controlling and optimizing the injection process as it provides useful information regarding the injector wells, such as the health of the injector wells and whether the injection process should be modified. Such modifications can include modification(s) of the injection fluid distribution system, modification(s) at the head of a given injector well, and/or modifications along the injector portion of a given injector well.

Figure 4:
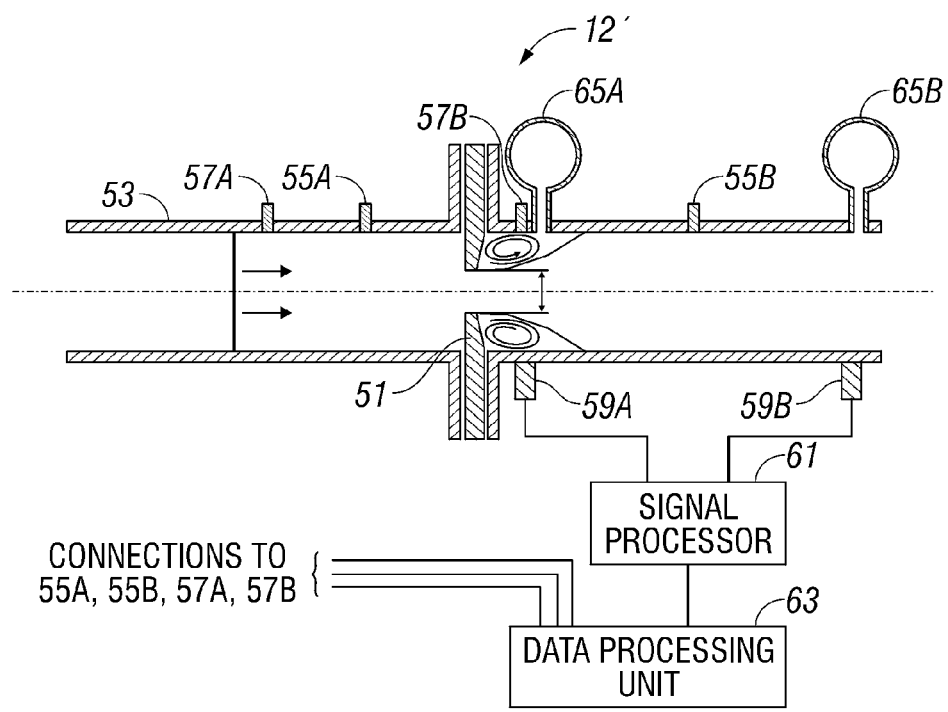
FIG. 4 is a schematic diagram of a metering device for determining fluid properties of a two phase fluid: the metering device can be used as part of the system of FIG. 3 to determine fluid properties of a two phase fluid upstream of the injector portion of the wellbore.

FIG. 4 is a diagram of an illustrative embodiment of a metering device 12' which can be used in the system of FIG. 3. The metering device 12' includes a restriction element 51 (such as an orifice plate or a flow nozzle) for restricting the flow of a two phase fluid flowing, through a tubular member 53 by decreasing the cross sectional area of the tubular member 53. When used as part of the system of FIG. 3, the tubular member 53 is fluidly coupled between a source of two phase fluid and the tubing 14 that extends down the injector well. A temperature sensor 55A mounted upstream of the restriction element 51 and a temperature sensor 55B, which is preferably mounted to the tubular member 53 downstream of the restriction element 51 after mixing of the two phase fluid as shown, measure the temperature of the two phase fluid flowing, through the tubular member 53. Pressure transducers 57A and 57B, which are preferably mounted to the tubular member 53 on opposite sides of the restriction element 51, measure the pressure drop of the two phase fluid across the restriction element 51. Sonic transceivers 59A 59B are supported by the tubular member 53 and spaced apart from one another along the length of the tubular member 53. The Sonic transceivers 59A, 59B are preferably disposed downstream of the restriction element 51 where better mixing of the two phase fluid is achieved. The sonic transceivers 59A, 59B are coupled to a signal processor 61 that is adapted to derive time-of-flight measurements for sonic pulses in the two phase fluid flowing through the tubular member 53. More particularly, Sonic transceiver 59A is controlled to emit a first sonic pulse train into the two phase fluid, which is received by sonic transceiver 59B. The first sonic pulse train propagates in the direction of flow for the two phase fluid in the tubular member 53.

The signal processor 61 measures the time of flight (sometimes referred to as "transmit time") of the pulses of the first Sonic pulse train. Sonic transceiver 59B is controlled to emit a second sonic pulse train into the two phase fluid, which is received by sonic transceiver 59A. The second sonic pulse train propagates counter to the direction of flow for the two phase fluid in the tubular member 53. The signal processor 61 measures the time of flight of the pulses of the second sonic pulse train. The signal processor 61 digitizes the time of flight measurements for the first and second sonic pulse trains and communicates such measurements (in digital form) to the data processing unit 63, which stores the time-of-flight data for both the first and second sonic pulse trains. The data processing unit 63 also interfaces to the sensors 55A, 55B, 57A, 57B, and stores the temperature and pressure measured by the sensors 55A, 55B, 57A, 57B (in digital form). The data processing unit 63 is adapted to calculate speed of sound in the two phase fluid as well as a vapor phase fraction α for the two phase fluid utilizing the stored time of flight data and the temperature and pressure measured by the sensors 55B, 57A, 57B as follows.

The time-of-flight $T_1$ of the pulses of the first sonic pulse train is given by the following equation:

$$T_1 = \frac{L}{c + u_x} \quad (13)$$

where L is the distance between the transceivers 59A, 59B.
c is the speed of sound in the two phase fluid, and
$u_x$ is the homogeneous velocity of the two phase fluid.

The time-of-flight $T_2$ for the pulses of the second sonic pulse train is given by the following:

$$T_2 = \frac{L}{c - u_x}. \quad (14)$$

Equation 13 may be combined with Equation 14 to cancel out the $u_x$ term and solve directly for c as follows:

$$\frac{1}{T_1} + \frac{1}{T_2} = \frac{2 \cdot c}{L} \quad (15)$$

$$c = \frac{L}{2}\left(\frac{1}{T_1} + \frac{1}{T_2}\right).$$

In this manner, the data processing unit 63 can calculate the speed of sound c in the two phase fluid from L (which is known) and the time of flight data $T_1$, $T_2$ for the first and second sonic pulse trains.

Finally, the speed of sound c is related to the vapor phase fraction α of the two phase fluid according to the equation:

$$c^2 \approx \frac{\rho_v c_v^2}{\alpha(1-\alpha)\rho_l} \quad (16)$$

where $\rho_v$ is the vapor phase density estimate of the two phase fluid at the measured temperature and pressure (determined from the equation of state), the pressure being measured downstream of the flow restrictor, in the region where the speed of sound is being measured:

$\rho_l$ is the liquid phase density estimate of the two phase fluid at the measured temperature and pressure (determined from the equation of state), measured locally as above; and $c_v$ is the speed of sound in the vapor phase of the two phase fluid under isothermal conditions, which is calculated according to the equation $$c_v = \frac{p}{\rho_v},$$

where p is the local pressure.

In this manner, the data processing unit 63 can calculate the vapor phase fraction α of the two phase fluid from the calculated speed of sound c and the temperature and pressures measured by the sensors 55B, 57A, 57B.

The data processing unit 63 is preferably adapted to perform the following:
- the calculations of step 250 as described above to derive the homogeneous density estimate of the two phase fluid from the vapor phase fraction α;
- the calculations of step 300 as described above to derive the volume flow rate of the two phase fluid from the vapor phase fraction and the homogeneous density estimate;
- the calculations of step 400 as described above to derive the mass flow rates of the vapor and liquid phases of the two phase fluid; and
- the calculations of step 500 to derive the enthalpy flux of the two phase fluid.

It is noted that Equation 16 assumes that mechanical and thermal equilibrium conditions are met, namely, that the pressure $p_v$ of the vapor phase of the fluid equals the pressure $p_l$ of the liquid phase of the fluid and the temperature $T_v$ of the vapor phase of the fluid equals the temperature $T_l$ of the liquid phase of the fluid. Equation 16 also assumes that the wavelengths of the first and second sound waves are significantly longer than the dimensions of the two phase structures in the flow such as bubbles and slugs.

The first and second sonic pulse trains generated by the sonic transceivers 59A and 59B may be reflected by surface structures within the tubular member 53 (or by other structures in the two phase flow). These reflections can interfere with the time of flight measurements carried out by the transceivers 59A, 59B and the signal processor 61. Two Helmholtz resonators 65A, 65B can be supported by the tubular member 53 in order to minimize such interference. The Helmholtz resonators 65A, 65B are located opposite the sonic transceivers 59A, 59B and resonate at a frequency that matches the wavelength of the sonic pulse train emitted from the corresponding transceiver. At resonance, the Helmholtz resonator presents low acoustic impedance such that the incident sonic pulses experience a phase inversion of one hundred-eighty degrees. By locating the Helmholtz resonators 65A, 65B approximately one wavelength away from the corresponding sonic transceiver, the reflected sound waves generated by the Helmholtz resonators 65A, 65B will appear as phase inverted signals with a delay of approximately two wave cycles to the original signals. As the first two cycles of the first and second sonic pulse trains are not affected by such reflection, the signal processor 61 can employ a matched filter (or cross-correlator) that detects the arrival of the respective sonic pulse train based on the detected signal of the first two cycles. Note that Helmholtz resonators 65A, 65B are optional parts of the metering device 12' when signal processing alone cannot remove the unwanted effects of reflected sound waves.

There have been described and illustrated herein several embodiments of a method, apparatus and system for determining the fluid properties of a two phase fluid. While particular embodiments of the invention have been described, it is not intended that the invention be limited thereto, as it is intended that the invention be as broad in scope as the art will allow and that the specification be read likewise. Thus, while particular steam injection applications have been disclosed, it will be appreciated that the present invention can be readily adapted for applications where monitoring and/or injection of a two phase fluid is required. It will therefore be appreciated by those skilled in the art that yet other modifications could be made to the provided invention without deviating from its scope as claimed.

What is claimed is:

1. In an injector well having a wellhead at the earth's surface where a two phase fluid is supplied to the injector well for injection into a surrounding formation along a portion of the injector well, a method for determining at least one fluid property of the two phase fluid along the portion of the injector well, the method comprising:
    measuring temperatures and pressures of the two phase fluid at the wellhead;
    measuring the speed of sound in the two phase fluid at the wellhead using time-of-flight measurements of sonic pulses passing through the two phase fluid;
    measuring temperatures of the two phase fluid at a plurality of locations along the portion of the injector well; and
    determining at least one fluid property of the two phase fluid along the portion of the injector well from the temperatures, pressures, and speed of sound measured at the wellhead, and the temperatures measured at the plurality of locations along the portion of the injector well, wherein the at least one fluid property is selected from the group including
        i) vapor phase fractions of the two phase fluid at the plurality of locations along the portion of the injector well;
        ii) changes in mass flow rate of the two phase fluid at the plurality of locations along the portion of the injector well;
        iii) enthalpy flux of the two phase fluid at the plurality of locations along the portion of the injector well; and
        iv) data, derived from a calculation of enthalpy flux upstream of the portion of the injector well, the calculation derived from a plurality of calculated fluid properties including
            a) a vapor phase fraction of the two phase fluid, derived in accordance with the equation $$c^2 \approx \frac{\rho_v c_v^2}{\alpha(1-\alpha)\rho_l^2}$$

where $\alpha$ is the vapor phase fraction of the two phase fluid;
$\rho_v$ is a vapor phase density estimate of the two phase fluid at the temperature and pressure measured at the wellhead;
$\rho_l$ is a liquid phase density estimate of the two phase fluid at the temperature and pressure measured at the wellhead; and
$c_v$ is the speed of sound in the vapor phase of the two phase fluid at the wellhead under isothermal conditions;

b) a homogeneous density estimate of the two phase fluid;
c) volume flow rate of the two phase fluid; and
d) mass flow rates of the vapor phase and liquid phase of the two phase fluid,
the data characterizing energy of the two phase fluid along the portion of the injector well.

2. A method according to claim 1, wherein;
the mass flow rates and the enthalpy flux of the two phase fluid at the plurality of locations along the portion of the injector well are derived from an equation that balances mass and energy of a unit volume, the equation being $$\frac{\rho(x+dx)}{\rho(x)} u_x(x+dx)\left(e(x+dx) - \frac{1}{2}u_x(x+dx)^2 - h(x)\right) = \frac{1}{2}u_x(x)^3 + \frac{\rho(x+dx)}{\rho(x)} u_x(x+dx)$$

where $\rho(x)$ is the homogeneous density of the two phase fluid at an entrance of the unit volume (at position x);
$\rho(x+dx)$ is the homogeneous density of the two phase fluid at an exit of the unit volume (at position x+dx);
$u_x(x)$ is the homogeneous velocity of the two phase fluid along the x direction of the injector well at the entrance of the unit volume;
$u_x(x+dx)$ is the homogeneous velocity of the two phase fluid along the x direction of the injector well at the exit of the unit volume;
$h(x)$ is the total enthalpy of the two phase fluid at the entrance of the unit volume; and
$e(x+dx)$ is the internal energy of the two phase fluid at the exit of the unit volume.

3. A method according to claim 1, wherein:
said homogeneous density estimate of the two phase fluid is derived in accordance with the equation $$\rho = \rho_v \alpha + \rho_l(1-\alpha),$$

where $\rho$ is said homogeneous density estimate of the two phase fluid;
$\alpha$ is the vapor phase fraction of the two phase fluid;
$\rho_v$ is a vapor phase density estimate of the two phase fluid at the temperature and pressure measured at the wellhead; and
$\rho_l$ is a liquid phase density estimate of the two phase fluid at the temperature and pressure measured at the wellhead.

4. A method according to claim 1, wherein:
said volume flow rate $Q_t$ of the two phase fluid is derived in accordance with the following equations $$u_2 = C_d \sqrt{\frac{2(h_1 - h_2)}{1 - \frac{\rho_2^2 A_2^2}{\rho_1^2 A_1^2}}}$$

where
$u_2$ is the homogeneous velocity of the two phase fluid at the vena contracta of a restriction element;
$C_d$ is a discharge coefficient;
$h_1$ is the enthalpy at the inlet of the restriction element;
$h_2$ is the enthalpy at the outlet of the restriction element;
$\rho_1$ is the homogeneous density upstream of the restriction element;

$\rho_2$ is the homogeneous density at the vena contracta of the restriction element;

$A_1$ is the cross sectional area of the two phase fluid flow upstream of the restriction element; and $A_2$ is the cross-sectional area of the two phase fluid flow at the vena contracta of the restriction element; and $Q_t = u_2 A_2$.

5. A method according to claim 1, wherein:

said mass flow rates of the vapor phase and liquid phase of the two phase fluid are derived in accordance with the following equations $\dot{m}_v = (\alpha \rho_v)_2 Q_t$ $\dot{m}_l = (\rho_l(1-\alpha))_2 Q_t$ where $\alpha$ is the vapor phase fraction of the two phase fluid;

$\rho_l$ is a liquid phase density estimate of the two phase fluid at the temperature and pressure measured at the wellhead;

$\rho_v$ is a vapor phase density estimate of the two phase fluid at the temperature and pressure measured at the wellhead; and $Q_t$ is the volume flow rate.

6. A method according to claim 1, wherein said two phase fluid comprises steam and water.

7. In an injector well having a wellhead at the earth's surface where a two phase fluid is supplied to the injector well for injection into a surrounding formation along a portion of the injector well, a system for determining at least one fluid property of the two phase fluid along the portion of the injector well, the system comprising:

means for measuring temperatures and pressures of the two phase fluid at the wellhead;

means for measuring the speed of sound in the two phase fluid at the wellhead using time-of-flight measurements of sonic pulses passing through the two phase fluid;

a tool, movable within the injector well, for measuring temperatures of the two phase fluid at a plurality of locations along the portion of the injector well; and means for determining at least one fluid property of the two phase fluid along the portion of the injector well from the temperatures, pressures, and speed of sound measured at the wellhead, and the temperatures measured by said tool, wherein the at least one fluid property of the two phase fluid is selected from the group including i) vapor phase fractions of the two phase fluid at the plurality of locations along the portion of the injector well;

ii) changes in mass flow rate of the two phase fluid at the plurality of locations along the portion of the injector well;

iii) enthalpy flux of the two phase fluid at the plurality of locations along the portion of the injector well; and iv) data, derived from output of a means for calculating enthalpy flux upstream of the portion of the injector well, wherein the means for calculating the enthalpy flux upstream of the portion of the injector well includes means for calculating a plurality of fluid properties including a) a vapor phase fraction of the two phase fluid, derived in accordance with the equation $$c^2 \approx \frac{\rho_v c_v^2}{\alpha(1-\alpha)\rho_l^2},$$

where $\alpha$ is the vapor phase fraction of the two phase fluid;

$\rho_v$ is a vapor phase density estimate of the two phase fluid at the temperature and pressure measured at the wellhead;

$\rho_l$ is a liquid phase density estimate of the two phase fluid at the temperature and pressure measured at the wellhead; and $c_v$ is the speed of sound in the vapor phase of the two chase fluid at the wellhead under isothermal conditions b) a homogeneous density estimate of the two phase fluid;

c) volume flow rate of the two phase fluid; and d) mass flow rates of the vapor phase and liquid phase of the two phase fluid, the data characterizing energy of the two phase fluid along the portion of the injector well.

8. A system according to claim 7, wherein;

the mass flow rates and the enthalpy flux of the two phase fluid at the plurality of locations along the portion of the injector well are derived from an equation that balances mass and energy of a unit volume, the equation being $$\frac{\rho(x+dx)}{\rho(x)} u_x(x+dx)\left(e(x+dx) - \frac{1}{2}u_x(x+dx)^2 - h(x)\right) = \frac{1}{2}u_x(x)^3 + \frac{\rho(x+dx)}{\rho(x)} u_x(x+dx)$$

where $\rho(x)$ is the homogeneous density of the two phase fluid at an entrance of the unit volume (at position x);

$\rho(x+dx)$ is the homogeneous density of the two phase fluid at an exit of the unit volume (at position x+dx);

$u_x(x)$ is the homogeneous velocity of the two phase fluid along the x direction of the injector well at the entrance of the unit volume;

$u_x(x+dx)$ is the homogeneous velocity of the two phase fluid along the x direction of the injector well at the exit of the unit volume;

$h(x)$ is the total enthalpy of the two phase fluid at the entrance of the unit volume; and $e(x+dx)$ is the internal energy of the two phase fluid at the exit of the unit volume.

9. A system according to claim 7, wherein:

said homogeneous density estimate of the two phase fluid is derived in accordance with the equation $\rho = \rho_v \alpha + \rho_l (1-\alpha)$, where $\rho$ is said homogeneous density estimate of the two phase fluid;

$\alpha$ is the vapor phase fraction of the two phase fluid;

$\rho_v$ is a vapor phase density estimate of the two phase fluid at the temperature and pressure measured at the wellhead; and $\rho_l$ is a liquid phase density estimate of the two phase fluid at the temperature and pressure measured at the wellhead.

10. A system according to claim 7, wherein:
said volume flow rate $Q_t$ of the two phase fluid is derived in accordance with the following equations $$u_2 = C_d \sqrt{\frac{2(h_1 - h_2)}{1 - \frac{\rho_2^2 A_2^2}{\rho_1^2 A_1^2}}}$$

where
$u_2$ is the homogeneous velocity of the two phase fluid at the vena contracta of a restriction element;
$C_d$ is a discharge coefficient;
$h_1$ is the enthalpy at the inlet of the restriction element;
$h_2$ is the enthalpy at the outlet of the restriction element;
$\rho_1$ is the homogeneous density upstream of the restriction element;
$\rho_2$ is the homogeneous density at the vena contracta of the restriction element;
$A_1$ is the cross sectional area of the two phase fluid flow upstream of the restriction element; and
$A_2$ is the cross-sectional area of the two phase fluid flow at the vena contracta of the restriction element; and $Q_t = u_2 A_2$.

11. A system according to claim 7, wherein:
said mass flow rates of the vapor and liquid phases of the two phase fluid are derived in accordance with the following equations $\dot{m}_v = (\alpha \rho_v)_2 Q_t$ $\dot{m}_l = (\rho_l(1-\alpha))_2 Q_t$ where
$\alpha$ is the vapor phase fraction of the two phase fluid;
$\rho_l$ is a liquid phase density estimate of the two phase fluid at the temperature and pressures measured at the wellhead;
$\rho_v$ is a vapor phase density estimate of the two phase fluid at the temperature and pressure measured at the wellhead; and
$Q_t$ is the volume flow rate.

12. A system according to claim 7, wherein said two phase fluid comprises steam and water.

13. A system according to claim 7, further comprising telemetry means for communicating measurements made by said tool to said determining means.

14. A system according to claim 13, further comprising coiled tubing that supports said tool within the injector well.

15. A system according to claim 14, wherein said tool is supported by the coiled tubing at its downhole end.

16. A system according to claim 14, wherein said coiled tubing houses at least one electrical cable and said telemetry means communicates data over said at least one electrical cable.

* * * * *